(12) United States Patent
Itoyama et al.

(10) Patent No.: US 7,019,032 B2
(45) Date of Patent: Mar. 28, 2006

(54) AGENT FOR TREATING PARKINSON'S DISEASE COMPRISING ASTROCYTE FUNCTION-IMPROVING AGENT AS ACTIVE INGREDIENT

(75) Inventors: Yasuto Itoyama, Miyagi (JP); Hiroyuki Kato, Miyagi (JP); Tsutomu Araki, Miyagi (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/906,065

(22) Filed: Jul. 17, 2001

(65) Prior Publication Data

US 2002/0032185 A1 Mar. 14, 2002

(30) Foreign Application Priority Data

Jul. 18, 2000 (JP) .......................... P. 2000-216763

(51) Int. Cl.
*A61K 31/20* (2006.01)
(52) U.S. Cl. ....................................... 514/558; 514/557
(58) Field of Classification Search ................ 514/557, 514/558
See application file for complete search history.

(56) References Cited

U.S. PATENT DOCUMENTS

| | | | |
|---|---|---|---|
| 5,240,662 A | | 8/1993 | Erdos et al. |
| 5,672,746 A | * | 9/1997 | Nau et al. .................... 562/598 |
| RE37,670 E | | 4/2002 | Nau et al. |

FOREIGN PATENT DOCUMENTS

| | | | |
|---|---|---|---|
| EP | 0 632 008 A1 | | 1/1995 |
| EP | 0 632 008 B1 | | 1/1995 |
| JP | 632008 A1 | * | 5/1994 |
| JP | 07 316092 A | | 12/1995 |
| RU | 2 076 700 | | 4/1997 |

OTHER PUBLICATIONS

DiPiro et al., Editor-in-Chief, Pharmacotherapy, A Pathophysiologic Approach, Chapter 42, Parkinson's Disease, pp. 632-641, 1989.*

Stedman's Medical Dictionary, 25th Edition, Illustrated, pp. 1256, 1268 1994.*
Webster's II, New Riverside University Dictionary, p. 933, 1988.*
M. Kohutnicka, et al, "Microglial and Astrocytic Involvement in a Murine Model of Parkinson's Disease Induced by 1-Methyl-4-Phenyl,-1,2,3,6-Tetrahydropyridine (MPTP)," *Immunopharmacology*, Elsevier Science Publishers BV, XX, vol. 39, No. 3, 1998, pp. 167-180.
B. Mirza, et al, "The absence of reactive astrocytosis is indicative of a unique inflammatory process in Parkinson's disease," Database Embase 'Online!, Elsevier Science Publishers, XP002182465, Abstract, & Neuroscience, (1999) 95/2, (425-432).
D. L. Montgomery, "Astrocytes: form, functions, and roles in disease," Database Medline 'Online!, U.S. national Library of Medicine (NLM), Bethesda, MD, XP002182466, Abstract, & Veterinary Pathology, (Mar. 1994) 31 (2), 145-67.
Patent Abstracts of Japan, JP 07-316092, date Dec. 5, 1995.
XP-002182465—Abstract (1999).
XP-002182466—Abstract (/1994).
Malgorzata Kohutnicka et al., Microglial and Astrocyctic Involvement in a Murine Model of Parkinson's Disease Induced by 1-methyl-4-phenyl-1,2,3,6-tetrahydropyridine (MPTP), (1998), pp. 167-180.

* cited by examiner

*Primary Examiner*—Dwayne Jones
(74) *Attorney, Agent, or Firm*—Sughrue Mion, PLLC

(57) ABSTRACT

An agent for preventing and/or treating Parkinson's disease or Parkinson's syndrome, comprising, as an active ingredient, an astrocyte function-improving agent is disclosed. The astrocyte function-improving agent is preferably a compound represented by formula (I), a non-toxic salt thereof, or a hydrate thereof:

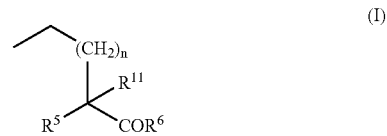

(I)

$R^5$, $R^6$, $R^{11}$ and n are defined in the specification.

2 Claims, No Drawings

AGENT FOR TREATING PARKINSON'S DISEASE COMPRISING ASTROCYTE FUNCTION-IMPROVING AGENT AS ACTIVE INGREDIENT

BACKGROUND OF THE INVENTION

1. Filed of the Invention

The present invention relates to remedies for Parkinson's disease.

More particularly, the present invention relates to an agent for treating and/or preventing Parkinson's disease or Parkinson's syndrome, comprising, as an active ingredient, an astrocyte function-improving agent represented by formula (I), a non-toxic salt thereof or a hydrate thereof:

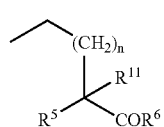
(I)

wherein the meaning of each symbol will be defined hereinafter.

2. Discussion of the Background

Parkinson's disease is a neurodegenerative disease which has been designated as one of specialization diseases by the Ministry of Health and Welfare in Japan. Concerning the clinical symptoms of Parkinson's disease, there are observed three large characteristics, i.e., 1) tremor, 2) akinesia and 3) rigidity. Since it was found that the dopamine content was reduced in the brain of patients with Parkinson's disease, it is considered that a decrease in dopamine in the brain causes Parkinson's disease. Therefore, the treatment of Parkinson's disease is carried out by administering dopamine with a form of precursor, regulating the dopamine metabolism or using dopamine agonist.

There have been known several remedies for Parkinson's disease, and typical examples include L-dopa (dopamine precursor), dopamaine agonists, anticholinergic drugs, dopamine release promoters (amantadine etc.) and monoamine oxidase B inhibitors (selegiline etc.). However, these drugs suffer from some problems, such as a decline of the drug effect after prolonged administration, side effects, a failure to prevent the progress of the disease and the like, and thus therapeutic benefit obtained with antiparkinsonian drugs available at present is insufficient.

Parkinson's syndrome means a group of nervous diseases including Parkinson's disease which exhibit conditions similar to Parkinson's disease (i.e., the three symptoms as described above).

On the other hand, it is stated in JP-A-7-316092 (the term "JP-A" as used herein means an "unexamined published Japanese patent application") that compounds represented by formula (I) have effects of improving brain functions (in particular, astrocyte function) and therefore are useful in treating and preventing Alzheimer's disease, amyotrophic lateral sclerosis, progressive supranuclear palsy, olivopontocerebellar atrophy, neuronal dysfunction by stroke or traumatic injury, multiple sclerosis, astrocytoma, meningitis, brain abscess, Creutzfeldt-Jakob disease, AIDS dementia etc.

SUMMARY OF THE INVENTION

An object of the present invention is to provide an agent for Parkinson's disease.

This and other objects of the present invention have been attained by an agent for preventing and/or treating Parkinson's disease or Parkinson's syndrome, comprising, as an active ingredient, an astrocyte function-improving agent.

DETAILED DESCRIPTION OF THE INVENTION

The astrocyte function-improving agent is preferably a compound represented by formula (I), a non-toxic salt thereof, or a hydrate thereof:

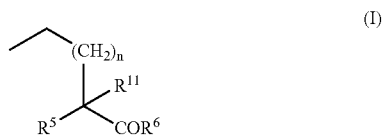
(I)

wherein $R^6$ represents hydroxy, C1–4 alkoxy, C1–4 alkoxy substituted with one phenyl, or —$NR^9R^{10}$, wherein $R^9$ and $R^{10}$ each independently represent:
(i) hydrogen,
(ii) C1–4 alkyl,
(iii) phenyl,
(iv) phenyl substituted with C1–4 alkoxy or carboxyl,
(v) a 4- to 7-membered heterocyclic ring containing one nitrogen atom, or
(vi) C1–4 alkyl substituted with phenyl,
    C1–4 alkyl substituted with C1–4 alkoxy- or carboxyl-substituted phenyl,
    C1–4 alkyl substituted with a 4- to 7-membered heterocyclic ring containing one nitrogen atom,
(vii) a 4- to 7-membered heterocyclic ring having 1 or 2 nitrogen atoms or a 4- to 7-membered heterocyclic ring having one nitrogen atom and one oxygen atom, together with the nitrogen atom to which they are bonded,
(viii) an amino acid residue together with the nitrogen atom to which they are bonded;

(1) n is 1;
  $R^{11}$ represents hydrogen; and
  $R^5$ represents (C1–10 alkyl in which one of the carbon atom(s) is substituted with 1 to 3 fluorine atoms)-$CH_2$—,
  with the proviso that $R^5$ does not represent F—$(CH_2)_5$—, F—$(CH_2)_6$—, F—$(CH_2)_7$— and $F_3C$—$(CH_2)_2$—; or (2) n is 0 or 1;
  $R^{11}$ represents hydrogen or chlorine; and
  $R^5$ represents:
  C3–10 alkyl,
  C3–10 alkenyl,
  C2–10 alkoxy,
  C2–10 alkylthio,
  C3–7 cycloalkyl,
  phenyl,
  phenoxy,
  F—$(CH_2)_m$, in which m is an integer of 5 to 7,
  $F_3C$—$(CH_2)_2$—,
  (C2–10 alkyl substituted with 1 or 2 chlorine atoms)-$CH_2$, or (C1–5 alkyl substituted with 1 or 2 substituents selected from the group consisting of C1–4 alkoxy, C3–7 cycloalkyl, phenyl and phenoxy)-CH$_2$—; or $R^5$ and $R^{11}$, taken together, form C3–10 alkylidene.

JP-A-7-316092 discloses that the compounds represented by formula (I) have an effect of improving astrocyte function and thus are effective for Alzheimer's disease etc. However, there is no described that these compounds are effective for Parkinson's disease and Parkinson's syndrome. Although the presence of reactive astrocytes was confirmed in Parkinson's disease (*Greenfield's Neuropathology*, 6th edition, Graham D L, Lantos P L (eds), Arnold, London, 1997), it has not been decided so far either these reactive astrocytes causes Parkinson's disease or are formed as the result thereof. It has been confirmed for the first time by the present invention that the compounds represented by formula (I) are effective in an experiment in vivo (Parkinson's disease model).

In a preferred embodiment, the astrocyte function-improving agents for use in the present invention are a compound of the formula (I) wherein n is 1, R11 is hydrogen, R5 is C3–10 alkyl and R6 is hydroxy and non-toxic salts thereof.

In a more preferred embodiment, the astrocyte function-improving agents for use in the present invention are (R)-2-propyloctanoic acid and non-toxic salts thereof. However, it is fully expected that not only (R)-2-propyloctanoic acid, which is a typical example of the compounds according to the present invention, but any compounds represented by formula (I) are effective for Parkinson's disease because they have the effect of improving the astrocyte function.

The compounds represented by formula (I) are publicly known per se or can be produced by the method described in U.S. Patent Publication No. 2003/0096802 A1, corresponding to JP-A-7-316092 or U.S. Pat. No. 6,608,221, corresponding to WO 00/48982.

The compounds for use in the present invention can be converted into the corresponding salts by publicly known methods. Non-toxic and water-soluble salts are preferred. Examples of suitable salts include salts of alkali metals (potassium, sodium etc.), salts of alkaline earth metals (calcium, magnesium etc.) and salts of pharmaceutically acceptable amines (tetramethylammonium, triethylamine, methylamine, dimethylamine, cyclopentylamine, benzylamine, phenethylamine, piperidine, monoethanolamine, diethanolamine, tris(hydroxymethyl)amine, lysine, arginine, N-methyl-D-glucamine etc.). The sodium salts are particularly preferred.

The compounds to be used in the present invention can be converted into the corresponding acid addition salts by publicly known methods. Non-toxic and water-soluble acid addition salts are favorable. Examples of appropriate acid addition salts include inorganic acid salts such as hydrochlorides, hydrobromides, hydroiodides, sulfates, phosphates and nitrates, and organic acid salts such as acetates, lactates, tartarates, oxalates, fumarates, maleates, citrates, benzoates, methanesulfonates, ethanesulfonates, benzenesulfonates, toluenesulfonates, isethionates, glucuronates and gluconates.

The compounds according to the present invention or salts thereof can be converted into hydrates by publicly known methods.

Pharmacological Activity:

Because of having an effect of improving the astrocyte function, the compounds of the present invention represented by formula (I) are efficacious in a Parkinson's disease model as will be described hereinafter. Thus, it is expected that these compounds are effective for Parkinson's disease and Parkinson's syndrome.

Toxicity:

It has been confirmed that the compounds of the present invention represented by formula (I) have such low toxicity as being sufficiently safe in using as drugs. When (R)-2-propyloctanoic acid was intravenously administered to dogs in a single dose of 100 mg/kg, for example, no case of death was observed.

Application to Drugs:

The astrocyte function-improving agents for use in the present invention, salts thereof or hydrates of the same are useful in treating and/or preventing Parkinson's disease or Parkinson's syndrome.

For the purpose above described, the astrocyte function-improving agents, a salt thereof, or a hydrate thereof may be normally administered to human or animal systemically or locally and orally or parenterally.

The doses to be administered are determined depending upon age, body weight, symptom, the desired therapeutic effect, the route of administration, and the duration of the treatment etc. In the human adult, the doses per person per dose are generally between 1 mg and 1000 mg, by oral administration, up to several times per day, and between 0.1 mg and 100 mg, by subcutaneous, intravenous or intranasal administration up to several times per day, or by continuous administration between 1 and 24 hours per day into vein.

As mentioned above, the doses to be used depend upon various conditions. Therefore, there are cases in which doses lower than or greater than the ranges specified above may be used.

The compounds of the present invention may be administered as inner solid compositions or inner liquid compositions for oral administration, or as injections, liniments or suppositories etc. for parenteral administration.

Inner solid compositions for oral administration include compressed tablets, pills, capsules, dispersible powders and granules etc. Furthermore, they also include gargling agents and sublingual agents for intraoral insertion and adsorption. Capsules contain hard capsules and soft capsules.

In such inner solid compositions, one or more of the active compound(s) are prepared as pharmaceuticals by known methods as they are, or by mixing with an inert diluent (lactose, mannitol, glucose, microcrystalline cellulose, starch etc.), connecting agents (hydroxypropyl cellulose, polyvinylpyrrolidone, magnesium metasilicate aluminate etc.), disintegrating agents (cellulose calcium glycolate etc.), lubricating agents (magnesium stearate etc.), stabilizing agents, assisting agents for dissolving (glutamic acid, asparaginic acid etc.) etc. If necessary, the pharmaceuticals may be coated with a coating agent (sugar, gelatin, hydroxypropyl cellulose, hydroxypropyl cellulose phthalate etc.), or be coated with two or more films. Furthermore, capsules of absorbable materials such as gelatin are also included.

Inner liquid compositions for oral administration include pharmaceutically acceptable water agents, suspensions, emulsions, syrups, elixirs etc. In such liquid compositions, one or more of the active compound(s) are dissolved, suspended or emulsified in inert diluent(s) generally used (purified water, ethanol, mixture thereof etc.). Furthermore, the liquid compositions may also contain wetting agents, suspending agents, emulsifying agents, sweetening agents, flavouring agents, perfuming agents, preserving agents, buffer agents etc.

Injections for parenteral administration include solutions, suspensions, emulsions, and solid injections which are dissolved or suspended in solvent(s) when they are used. One or more active compound(s) are dissolved, suspended or emulsified in solvent(s) when such compositions are used. Examples of the solvents include distilled water for injection and physiological salt solution, plant oil, propylene glycol, polyethylene glycol and alcohol such as ethanol etc., and mixture thereof. Such compositions may contain stabilizing agent, assisting agents for dissolving (glutamic acid, asparaginic acid, POLYSOLBATE80 (registered trade mark) etc.), suspending agents, emulsifying agents, dispersing agents, buffer agents, preserving agents etc. They are manufactured and prepared by sterilization at the final step or aseptic treatment. They may also be manufactured in the form of sterile solid compositions, such as freeze-drying products, and they can be dissolved in sterilized or sterile distilled water for injection or other solvent before use.

Now, the present invention will be described in greater detail by reference to the following Examples. However, it is to be understood that the present invention is not construed as being limited thereto.

EXAMPLE 1

Improvement Effect of the Compound of the Present Invention in Experimental Model of Parkinson's Disease Induced by Administration of MPTP:

Male C57BL/6 mice (body weight: 20 to 28 g) were divided into groups each having 6 to 12 animals. Without anesthetizing, MPTP (10 mg/kg; 1-methyl-4-phenyl-1,2,3,6-tetrahydropyridine hydrochloride) was intraperitoneally administered to the mice 4 times at intervals of 1 hour (*Brain Res.*, 824: 224–231 (1999)). To the models thus prepared, Compound A of the present invention ((R)-2-propyloctanoic acid) was administered after 1, 6, 24 and 48 hours. Three days after the final administration, striata of the mice were collected. After weighing, the striata were immediately frozen and stored. Then, dopamine content and DOPAC (3,4-dihydroxypyenylacetate) content were measured by HPLC in a conventional manner and evaluated. Table 1 shows the results.

Dunnett's multiple comparison test (both sides) was performed on the basis of the data of the group with the administration of MPTP alone.

The values in Table 1 are shown by the average ± the standard deviation.

TABLE 1

|  | Dopamine content($\mu$g/g) | DOPAC content ($\mu$g/g) |
|---|---|---|
| Control (physiological saline) | 13.32 ± 2.34** | 2.50 ± 0.38** |
| Compound A of invention 30 mg/kg | 12.17 ± 1.41** | 2.97 ± 0.49** |
| MPTP | 2.96 ± 2.07 | 1.40 ± 0.78 |
| MPTP + compound A of invention 3 mg/kg | 4.13 ± 1.48 | 1.30 ± 0.31 |
| MPTP + compound A of invention 10 mg/kg | 5.45 ± 2.00* | 2.07 ± 0.77 |
| MPTP + compound A of invention 30 mg/kg | 6.75 ± 2.72** | 2.26 ± 0.52* |

*: $p < 0.05$, **: $p < 0.01$

Compared with the group of the administration of MPTP alone, the groups of the administration of MPTP+ the compound of the present invention showed significantly increased dopamine and DOPAC content depending on the dose. The data of the group with the compound of the present invention alone were almost the same as the data of the control group, which indicates that it showed no adverse effect when used alone in normal animals.

Also, the compounds of the present invention are efficacious even in post treatment administration, which makes them epoch-making drugs different from the existing ones.

FORMULATION EXAMPLE 1

Preparation of Capsules:

(R)-2-propyloctanoic acid (1 g) was encapsulated into gelatin capsules to obtain 10 capsules each containing 100 mg of the active ingredient.

This application is based on Japanese application No. 2000-216763, filed on Jul. 18, 2000, the entire content of which is incorporated herein by reference.

While the invention has been described in detail and with reference to specific embodiments thereof, it will be apparent to one skilled in the art that various changes and modifications can be made therein without departing from the spirit and scope thereof. All references cited herein are incorporated, by reference, in their entirety.

What is claimed is:

1. A method for treating Parkinson's disease or Parkinson's syndrome comprising administering an effective amount of (R)-2-propyloctanoic acid, a non-toxic salt thereof, or a hydrate thereof.

2. The method according to claim 1, wherein the Parkinson's disease or Parkinson's syndrome is tremor, akinesia or rigidity.

* * * * *